United States Patent
Ramzipoor et al.

(10) Patent No.: US 8,574,493 B2
(45) Date of Patent: *Nov. 5, 2013

(54) STERILIZATION METHODS AND APPARATUS

(71) Applicant: Amaranth Medical Pte., Singapore (SG)

(72) Inventors: Kamal Ramzipoor, Fremont, CA (US); Chang Y. Lee, Redwood City, CA (US); Fozan O. El-Nounou, Santa Clara, CA (US)

(73) Assignee: Amaranth Medical Pte., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 13/671,211

(22) Filed: Nov. 7, 2012

(65) Prior Publication Data

US 2013/0138197 A1   May 30, 2013

Related U.S. Application Data

(63) Continuation of application No. 12/649,044, filed on Dec. 29, 2009, now Pat. No. 8,309,023.

(60) Provisional application No. 61/145,932, filed on Jan. 20, 2009.

(51) Int. Cl.
*A61L 2/08* (2006.01)
*A61L 2/16* (2006.01)

(52) U.S. Cl.
USPC ............................. 422/28; 623/1.11; 604/523

(58) Field of Classification Search
USPC ................... 422/28, 292, 295, 297; 604/523; 623/1.11

See application file for complete search history.

(56) References Cited

U.S. PATENT DOCUMENTS

| | | |
|---|---|---|
| 8,309,023 B2 | 11/2012 | Ramzipoor et al. |
| 2005/0107738 A1 | 5/2005 | Slater et al. |
| 2007/0014686 A1 | 1/2007 | Arnold et al. |
| 2010/0185270 A1 | 7/2010 | Ramzipoor et al. |

FOREIGN PATENT DOCUMENTS

| | | |
|---|---|---|
| CN | 201061621 | 5/2008 |
| WO | WO 83/00447 | 2/1983 |
| WO | WO 98/29029 | 7/1998 |
| WO | WO 99/03677 | 1/1999 |
| WO | WO 2010/085314 | 7/2010 |

*Primary Examiner* — Sean E Conley
(74) *Attorney, Agent, or Firm* — Levine Bagade Han LLP

(57) ABSTRACT

Sterilization methods for implantable prostheses are described, where a polymeric stent may be sterilized, e.g., via ETO sterilization, at a temperature below a glass transition temperature of the stent. A separate delivery catheter may be sterilized separately and the stent and delivery catheter may then be combined in an aseptic, or semi-aseptic environment and sterilized as an assembled system such that the requirements for sterilizing the system are relatively lower. Additionally and/or alternatively, valve and filter assemblies may be used with an optional mandrel assembly for maintaining sterility of the internal components of a catheter system.

13 Claims, 6 Drawing Sheets

STERILIZATION METHODS AND APPARATUS

CROSS-REFERENCE TO RELATED APPLICATIONS

This application is a continuation of U.S. patent application Ser. No. 12/649,044 filed Dec. 29, 2009 which claims the benefit of priority to U.S. Prov. App. 61/145,932 filed Jan. 20, 2009, each of which is incorporated herein by reference in its entirety.

FIELD OF THE INVENTION

The present invention relates generally to methods and apparatus for sterilization of temperature sensitive medical devices, particularly catheter devices and implantable prostheses.

BACKGROUND OF THE INVENTION

There are several commonly known methods for terminal sterilization, including, dry heat, steam autoclave, ethylene oxide (EO) and radiation (gamma and E-beam). There are also newer sterilization options that utilize hydrogen peroxide ($H_2O_2$) vapor which are effective sterilization methods for highly resistant spore thrillers, non-spore forming bacteria and other microorganisms.

However, many of these traditional sterilization methods suffer from a number of limitations which reduce their effectiveness. For instance, the application of dry heat is typically conducted at 160-170° C. for a minimum of two hours but due to its high temperature requirement, its application is highly limited for temperature-sensitive devices and instruments.

Another sterilization method utilizes steam autoclave which is the oldest and typically most cost-effective method of sterilization used mostly for surgical instruments. The applied steam reaches 121-148° C. in a pressure chamber at 15 PSI. The sterilization period is dependent on the temperature and size of the load and can range from 10-60 minutes. Yet because this method utilizes relatively high temperatures, it is not well suited for heat sensitive materials, devices, and instruments.

Another methods utilizes Ethylene Oxide (ETO) gas for items that are heat or moisture sensitive. Although the operating temperature of this process is far below those of dry heat and steam autoclave sterilization, it may still be too high for a certain medical devices, namely bioabsorbable stents.

Gamma and E-beam sterilization is another method which uses radiation where the effect on polymeric materials is the same for both. Gamma and E-beam sterilization typically subjects devices to irradiation sterilization but polymeric devices, in particular, will inevitably be affected by the radiation and will experience changes in their polymer structure such as chain scission and cross-linking). These processes may lead to significant changes and compromise in the tensile strength, elongation at break, and yield strain of such polymeric devices. Furthermore, the exact changes in mechanical properties may not be immediately apparent as there can be some time delay in the development of these changes.

Another sterilization further includes Vaporized Hydrogen Peroxide (VHP) sterilization which has been generally applied for sterilizing medical devices in hospitals worldwide. Sterilization by VHP occurs in to relatively low-moisture environment at a temperature less than 50 C. It is generally suitable for sterilizing heat and moisture-sensitive items and delicate instruments. Hydrogen Peroxide is an oxidizing agent that effects sterilization thru oxidation of key cellular components (e.g. membrane lipids, DNA, and other essential constituents). These chemical interactions at multiple biologically important reaction sites are believed to be responsible for the inactivation of microorganisms As a low-temperature gaseous method of sterilization, VHP is an alternative to ETO sterilization but VHP sterilization does not penetrate into the devices to be sterilized as much as ETO. However, besides low-temperature and moisture, VHP sterilization does offer other significant advantages over ETO sterilization including excellent material compatibility and short cycle, time. Yet like other sterilization modalities, VHP has limitations. Because VHP sterilization lacks the penetration available with ETO, an open gas pathway must be present. Medical devices such as PTCA or PTA catheters with or without stents mounted on to the delivery catheters may comprise relatively long tubular members in a range of 100-150 cm with luminal diameters as small as 0.008". Such configurations present a significant challenge for this method of sterilization as VHP sterilization is generally incapable of penetrating and sterilizing though these lumen lengths.

Because of these limitations, there is a need for a method that is capable of sterilizing devices with complex geometry and high-sensitivity to temperature and radiation exposure.

SUMMARY OF THE INVENTION

Bioabsorbable polymeric stents are especially sensitive to temperature, radiation, and moisture present in traditional sterilization processes. It is known that temperatures used during sterilization, e.g., ETO sterilization, can result in cracking of polymeric stent struts during stent deployment due to onset of brittle behavior.

In one embodiment, the stent may be constructed of a bioabsorbable polymeric material with a $T_g$ (glass transition temperature) between 40-80° C. While in an expanded form, this stent may be first exposed to an UFO sterilization process with, e.g., an operating temperature range of 38°-50° C. and with a relative humidity (RH) of 20%-80%. Since this sterilization temperature is at or below the $T_g$ of the stent material, undesirable thermal effects and deterioration of mechanical properties may be largely avoided. The stent may be subsequently crimped on to a pre-sterilized catheter delivery system in an aseptic or semi-aseptic environment. The assembly may then undergo a terminal sterilization step utilizing, e.g., a vaporized hydrogen peroxide (VHP) sterilization method. Because of the low temperature and RH levels of the VHP sterilization process, mechanical properties of the stent may not be adversely affected. To further preserve mechanical properties of stent, an example of the VHP sterilization process parameters may be set as follows: (1) temperature range below 60° C., (2) cycle time of 1 hr-10 hrs, and (3) concentration of 50%-60% normal peroxide by weight.

Aside from ETO or VHP sterilization, a nitrous oxide based sterilization method may also be utilized such as those commercially available from Noxilizer (Bethesda, Md.). The catheter assembly may be exposed to nitrous oxide, e.g., from 10 minutes to 1 hour and at a maximum temperature of 23° C. The exposure time can be increased as necessary to ensure complete device sterilization.

Another embodiment for maintaining the sterility of catheter lumens may incorporate the use of one or more microporous filters (e.g., 0.2 µm pore filters) coupled to a valve. A luer assembly having one or more valves (in either an opened or closed configuration) and filters coupled thereto may be used for sterilizing the catheter assembly. Furthermore, a mandrel assembly may also be used for blocking the catheter guidewire lumen for use in sterilizing the catheter assembly.

An inflation valve assembly, e.g., unidirectional valve or stopcock having a stop or valve operable between a closed and opened configuration may have an inflation lumen filter assembly coupled to the balloon inflation lumen extending, from the luer assembly. Likewise, a guidewire valve assembly having a stop or valve may be coupled to the guidewire lumen. A guidewire lumen filter assembly may be coupled proximally to the valve assembly. Utilizing 0.2 µm or smaller pore filters may prevent the introduction of microbial contaminants into the catheter lumens.

A removable seal may be optionally placed upon the catheter distal end or inserted therein to also seal the distal portion of the catheter assembly. An example of such a removable seal may utilize a mandrel sized for insertion within, a guidewire lumen of the catheter. A flared seal portion which extends proximally over the mandrel may be attached near or at a distal end of the mandrel such that when the mandrel is inserted within the guidewire lumen through a distal opening, the flared seal portion may extend at least partially over the catheter distal tip and upon the catheter outer surface to form a seal effectively isolating the catheter lumen from the environment and preventing introduction of microbial contaminants into the lumen.

With the valve assemblies and their respective filters coupled securely to the luer assembly, respective stops may be turned or configured into an opened configuration such that the catheter lumens are in fluid communication with the environment through the filters. Sterilization of the internal catheter lumens may be then achieved utilizing any or the methods described herein, e.g., ETO sterilization, or any other suitable sterilization methods. Alternatively, the slops may be turned or configured into their closed configurations and sterilization of the internal catheter lumens may nonetheless be achieved using other sterilization methods, e.g., E-beam sterilization.

Once the sterilization of the catheter lumens has been completed, the catheter assembly may be moved into a controlled aseptic environment, such as a clean room, where one or both stops may be closed (if sterilized in their opened configuration, otherwise, they may be tell closed). With the proximal end of the catheter effectively isolated by the liter assembly and the distal end of the catheter effectively isolated by the mandrel assembly, the internal catheter lumens may maintain their sterility.

To place a stent upon the inflation balloon after catheter sterilization, the stop on the inflation valve assembly may be opened (or left opened) and air or another fluid may be passed through the filter to at least partially inflate the balloon. Because the inflation lumen was pre-sterilized, passing the air or fluid through the filter may maintain sterility of the lumen and balloon. The polymeric stent (which may be pre-sterilized) may be crimped upon the balloon and the stop may then be turned into its closed configuration to again effectively isolate and maintain the lumen sterility.

Optionally, if the catheter system requires any further inspection or testing, such as pressure testing for ensuring the absence of leaks, both the stops for respective inflation and guidewire lumens may be opened and coupled to an air or fluid source and pressurized. Because any air of fluid passes through the respective filter assemblies, sterility of the catheter lumens may still be maintained.

With the stent crimped the balloon and the internal catheter lumens sterilized, one or both filter assemblies may be removed and the catheter assembly packaged. The entire assembly (or the external components) may then be terminally sterilized utilizing any of the methods described herein. Prior to the catheter assembly being used by the physician, one or both valves may be removed by the physician prior to stent implantation.

Turning back now to pre-conditioning and/or sterilization processes, another variation is described which achieves or maintains particular post-sterilization mechanical properties of the stent. The implanted stent may desirably achieve or maintain mechanical characteristics which are either enhanced or at the least unaffected by the sterilization methods. For instance, the stent 10 may achieve or maintain at least one (and desirably all) of the following characteristics, e.g., a diameter increase by 5%-80% via the inflatable balloon 12 without fracture formation; may curve up to 180° about a 1 cm curvature radius without fracture formation; exhibit a percent reduction in axial length of between 10%-50% without fracture formation when placed under an axial load; exhibit a percent reduction in diameter of between 5%-70% without fracture formation when placed under a compressive load; and exhibit a 20% radial deformation when placed under a load of 0.1 N-5 N.

Depending on the molecular weight and crystallinity combination of the stent materials chosen, the fully sterilized stent may be able to maintain its original crystallinity of 25%-35% and a molecular weight of 259,000 g/mol to 2,120,000 g/mol while providing high radial strength (e.g., 0.1 N-5N per 1 cm length at 20% compression), withstanding considerable amounts of strain without fracturing (e.g., 150% strain), and exhibiting high fatigue life under physiological conditions (e.g, 10 million cycles under radial pulse load), 200,000-1 million cycles under axial compression and torsional loads.

Examples of stents and methods of processing stents having such mechanical properties which may be produced utilizing the sterilization processes herein are shown and described in further detail in U.S. patent application Ser. Nos. 12/143,659 filed Jun. 20, 2008 and 12/488,453 filed Jun. 19, 2009, each of which is incorporated herein by reference in its entirety.

In yet another variation, the balloon may be inflated and stent mounted onto the inflated balloon prior to pre-sterilization. The assembly may be then sterilized using ETO sterilization with an operating temperature range of 38-50° C. and RH of 20%-80%. The stent may be subsequently crimped on to the balloon in an aseptic or semi-aseptic environment and terminally sterilized by using VHP sterilization. The purpose of pre-sterilization of the inflated balloon is to eliminate the need for inflation during the crimping process, thus reducing the potential for introduction of bacterial load.

DETAILED DESCRIPTION OF THE INVENTION

Medical devices including catheter delivery devices and implantable stems must be able to withstand mechanical loads that are imposed during delivery to the treatment site (such as loads imposed during intravascular delivery) as well as post implantation. These loads may be in forms of pulsatile, torsional, axial, compressive and/or combination thereof with various frequencies and amplitudes depending upon the site of implantation. Stents should ideally maintain their scaffolding properties and structural strength and integrity under these loading conditions. Thus, any compromise of their physical properties during sterilization may result in a mechanical failure pre or post implantation.

Bioabsorbable polymeric stents are especially sensitive to temperature, radiation, and moisture present in traditional sterilization processes. It is known that temperatures used during ETO sterilization can result in cracking of polymeric strut struts during stent deployment due to onset of brittle behavior.

Figure 1:
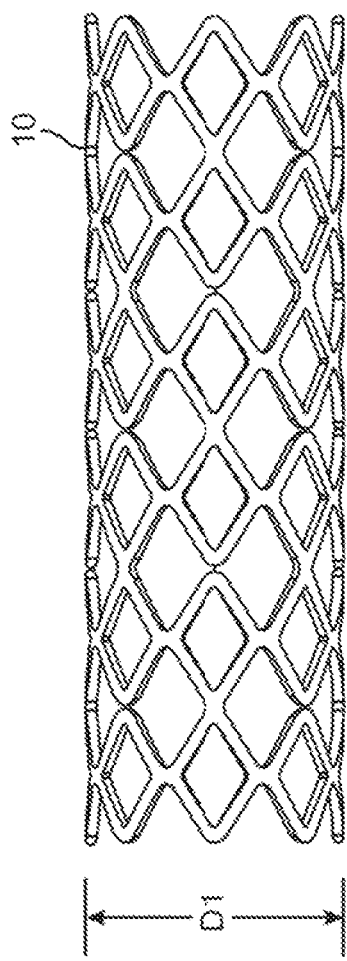
FIG. 1 shows a side view of an example of a polymeric stent which may be sterilized.

In one embodiment, the stent may be constructed of a bioabsorbable polymeric material with a $T_g$ (glass transition temperature) between 40-80° C. While in an expanded form, this stent may be first exposed to an ETO sterilization process with, e.g., an operating temperature range of 38°-50° C. and with a relative humidity (RH) of 20%-80%. Since this sterilization temperature is at or below the $T_g$ of the stent material, undesirable thermal effects and deterioration of mechanical properties may be largely avoided. FIG. 1 shows a side view of an example of a stent 10 having at a first diameter D1 which has been sterilized prior to assembly upon a catheter. Stent 10 may be subsequently crimped on to a pre-sterilized catheter delivery system in an aseptic or semi-aseptic environment. The final assembly from this process may result in bioburden levels of 0-1000 colony forming units (CFU), which is a measure of viable bacterial numbers.

Figure 2:
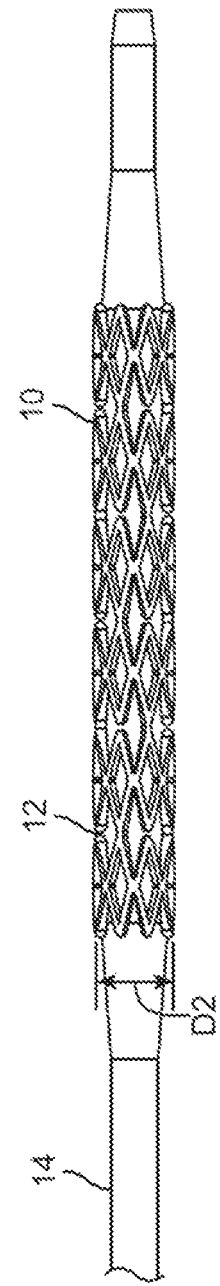
FIG. 2 shows a side view of a polymeric stent crimped upon a sterilized balloon assembly which may be sterilized as a system.

The assembly may then undergo a terminal sterilization step utilizing, e.g., a vaporized hydrogen peroxide (VHP) sterilization method. FIG. 2 shows a side view of the stent 10 crimped upon the delivery system, e.g., stent 10 may be assembled with delivery catheter 14 in an aseptic environment where stent 10 may be crimped upon an inflatable balloon 12 from its initial diameter D1 to a second smaller diameter D2. Because of the bacterial load present on the device is very low prior to this process, and also because certain components of the system which are challenging to sterilize (which may include the catheter lumen) has been pre-sterilized by conventional methods, the final VHP sterilization process may not require full penetration through the entire assembly (including the catheter lumen). Accordingly, such a sterilization process may be highly effective as a terminal process. Furthermore, because of the low temperature and RH levels of the VHP sterilization process, mechanical properties of the strut may not be adversely affected. To further preserve mechanical properties of stent, an example of the VHP sterilization process parameters may be set as follows: (1) temperature range below 60° C., (2) cycle time of 1 hr-10 hrs, and (3) concentration of 50%-60% normal peroxide by weight.

Aside from ETO or VHP sterilization, a nitrous oxide based sterilization method may also be utilized such as those commercially available from Noxilizer (Bethesda, Md.). The catheter assembly may be exposed to nitrous oxide, e.g., from 10 minutes to 1 hour and at a maximum temperature of 23° C. The exposure time can be increased as necessary to ensure complete device sterilization.

In order to maximize the sterilization potential of the nitrous oxide, sterilization of the catheter assembly could be accomplished in dual phases. The delivery system may be first sterilized using radiation. E-beam, or other method such as ETO sterilization. The stent may then be placed upon the sterilized catheter and the entire assembly may then be sterilized with nitrous oxide at heat levels no greater than room temperatures, e.g., 22° C. Because of the reduced heating levels, the reduced temperatures reduce the possibility of polymer material cross-linking and the polymer glass transition temperature is not impacted. Moreover, use of nitrous oxide may require less aeration time and will not impact any shape memory properties of the polymer steins.

As previously indicated, upon completion of the initial sterilization, the stent crimping process may be performed. The crimping process may involve the introduction of gases or fluids or other foreign materials (e.g., for balloon inflation) or tools such as mandrels into the internal lumens of the device. Yet introduction of foreign materials into a sterilized component may violate sterility of these areas. This may be especially problematic when the terminal sterilization does not have the capacity to penetrate through the walls of the device, e.g., through the catheter walls to sterilize these lumens.

Another embodiment for maintaining the sterility of catheter lumens may incorporate the use of one or more microporous filters (e.g., 0.2 μm pore filters) coupled to a valve. An example is shown in the side view of FIG. 3A which shows a side view of a luer assembly 20 having one or more valves (in either an opened or closed configuration) and filters coupled thereto for use in sterilizing the catheter assembly. FIG. 3B shows as partial cross-sectional side view of an inflation balloon assembly 12 coupled to the catheter 14 having luer assembly 20 and further having a mandrel assembly 38 blocking the catheter lumen for use in sterilizing the catheter assembly.

An inflation valve assembly 26, e.g., uni-directional valve or stopcock, having a stop or valve 28 operable between a closed and opened configuration may have an inflation lumen filter assembly 34, as described above, coupled to balloon inflation lumen 22 extending from luer assembly 20. Likewise, a guidewire valve assembly 30 (e.g., similar to valve assembly 26) having stop or valve 32 may be coupled to guidewire lumen 24. A guidewire lumen filter assembly 36

(e.g., similar to filter assembly 34) may be coupled proximally to valve assembly 30. Utilizing 0.2 μm pore filters 34, 36 may prevent the introduction of microbial contaminants into the catheter lumens.

A removable seal may be optionally placed upon the catheter distal end or inserted therein to also seal the distal portion of the catheter assembly. An example of such a removable seal is shown in mandrel assembly 38 which may utilize a mandrel 44 sized for insertion within a guidewire lumen 24 of catheter 14. A flared seal portion 46 which extends proximally over mandrel, 44 may be attached near or at a distal end of mandrel 44 along attachment 48 such that when mandrel 44 is inserted within guidewire lumen 24 through distal opening 40, flared seal portion 46 may extend at least partially over catheter distal tip 42 and upon the catheter outer surface to form a seal effectively isolating the catheter lumen 24 from the environment.

Figure 3A:
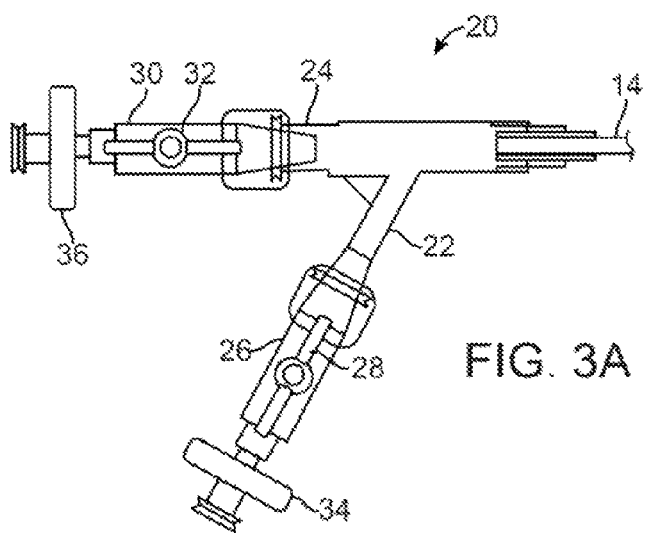
FIG. 3A shows a side view of a liter assembly having one or more valves (in either an opened or closed configuration) and filters coupled thereto far use in sterilizing the catheter assembly.
Figure 3B:
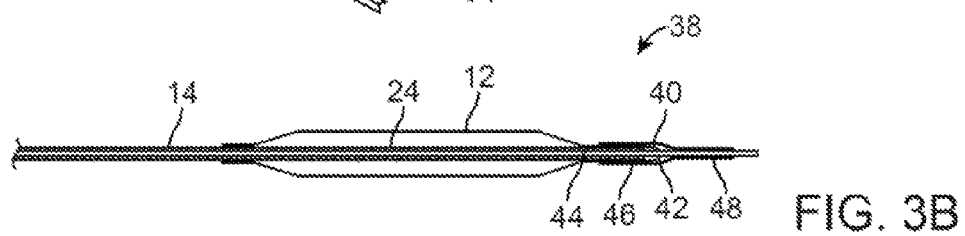
FIG. 3B shows a partial cross-sectional side view of an inflation balloon assembly coupled to a catheter and having a mandrel assembly blocking, the catheter lumen for use in sterilizing the catheter assembly.

With valve assemblies 26, 30 and their respective filters 34, 36 coupled securely to luer assembly 20, respective stops 28, 32 may be turned or configured into an opened configuration such that the catheter lumens are in fluid communication with the environment through filters 34, 36, as shown in FIG. 3A. Sterilization of the internal catheter lumens may be then achieved utilizing any of the methods described herein, e.g., ETO sterilization, or any other suitable sterilization methods. Alternatively, stops 28, 32 may be turned or configured into their closed configurations and sterilization of the internal catheter lumens may nonetheless be achieved using other sterilization methods, e.g., E-beam sterilization.

Once the sterilization of the catheter lumens has been completed, the catheter assembly may be moved into a controlled aseptic environment, such as a clean room, where one or both stops 28, 32 may be closed (if sterilized in their opened configuration, otherwise, they may be left closed). With the proximal end of the catheter 14 effectively isolated by luer assembly 20 and the distal end of catheter 14 effectively isolated by mandrel assembly 38, the internal catheter lumens may maintain their sterility.

Figure 4A:
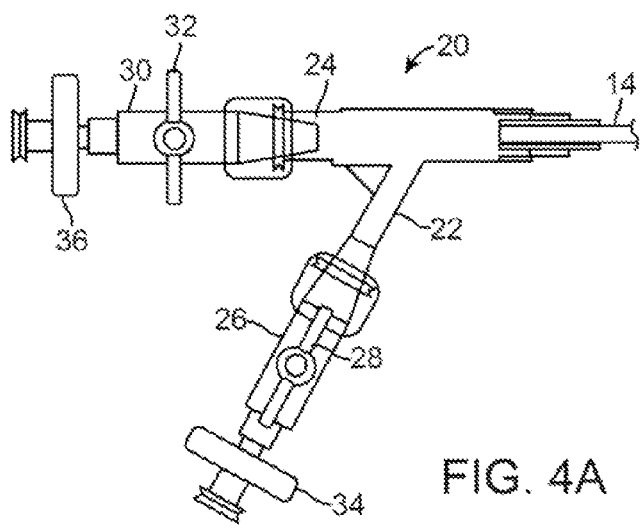
FIGS. 4A and 4B show respective luer (having an inflation lumen opened) and balloon assemblies with a polymeric stent crimped onto the balloon for sterilization.
Figure 4B:
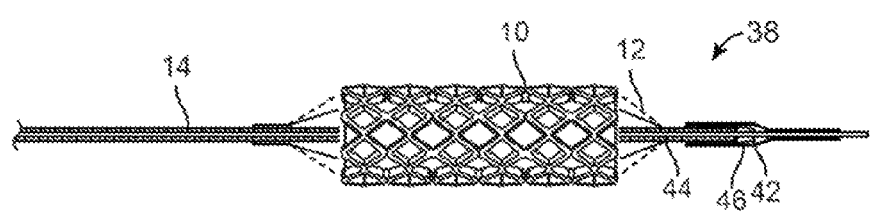

To place a stent upon the inflation balloon 12 after catheter sterilization, the stop 28 on inflation valve assembly 26 may be opened (or left opened) and air or another fluid may be passed through filter 34 to at least partially inflate balloon 12, as shown in respective FIGS. 4A and 4B. Because the inflation lumen 22 was pre-sterilized, passing the air or fluid through the filter 34 may maintain sterility of the lumen 22 and balloon 12. The polymeric stent 10 (which may be pre-sterilized) may be crimped upon the balloon 12, as shown in FIG. 4B, and stop 28 may then be turned into its closed configuration to again effectively isolate and maintain the lumen sterility.

Optionally, if the catheter system requires any further inspection or testing, such as pressure testing for ensuring the absence of leaks, both the stops 28, 32 for respective inflation and guidewire lumens 22, 24 may be opened and coupled to an air or fluid source and pressurized. Because any air of fluid passes through respective filter assemblies 34, 36, sterility of the catheter lumens may still be maintained.

Figure 5A:
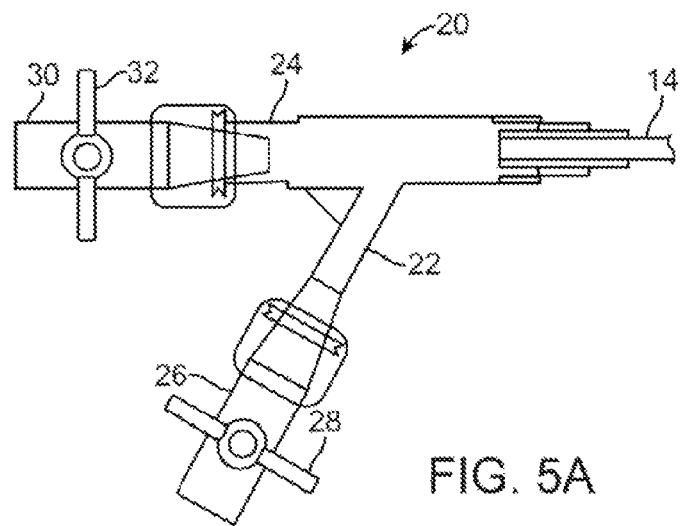
FIGS. 5A and 5B show respective luer (having the valves dosed and filters removed) and balloon assemblies fully sterilized.
Figure 5B:
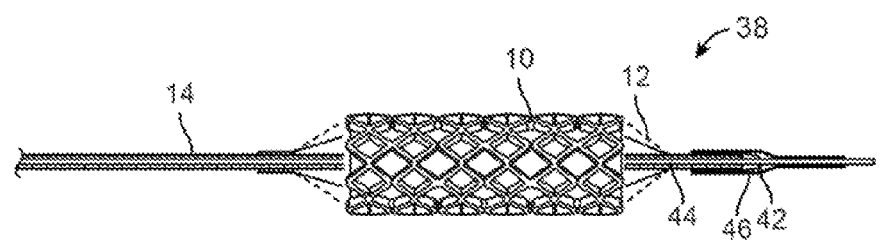
Figure 6A:
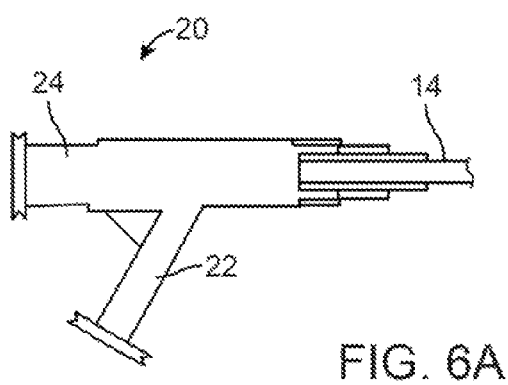
FIGS. 6A and 6B show respective luer (having valves removed) and balloon assemblies ready for use.
Figure 6B:
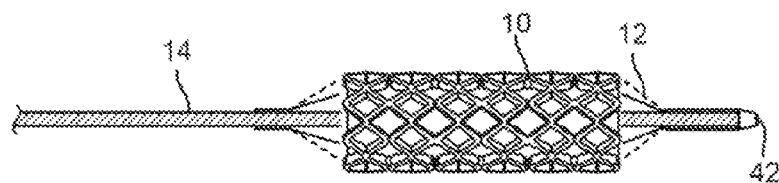

With the stent 10 crimped, the balloon 12 and the internal catheter lumens sterilized, one or both filter assemblies 34, 36 may be removed and the catheter assembly packaged, as shown in FIGS. 5A and 5B. The entire assembly (or the external components) may then be terminally sterilized utilizing any of the methods described herein. Prior to the catheter assembly being used by the physician, one or both valves 26, 30 (as well as mandrel assembly 38, if not already removed) may be removed by the physician prior to stent implantation, as shown in FIGS. 6A and 6B.

Figure 7A:
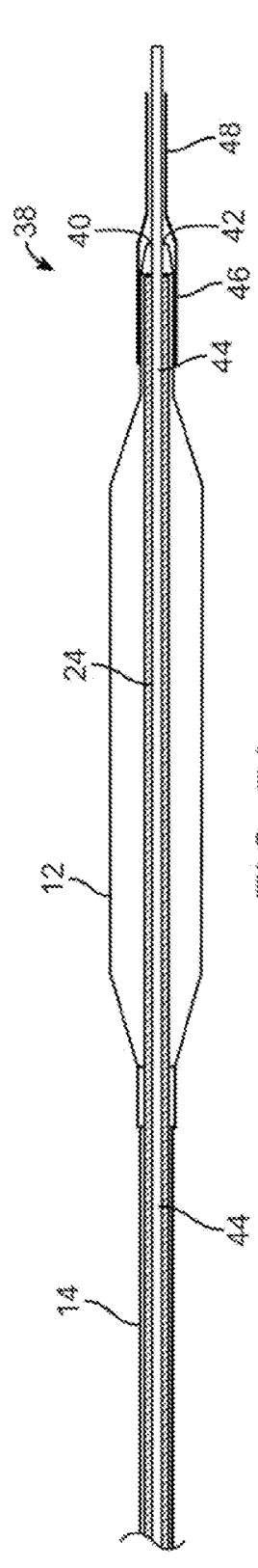
FIGS. 7A and 7B show partial cross-sectional side views of one variation of the mandrel assembly removed from the distal tip of the catheter.
Figure 7B:
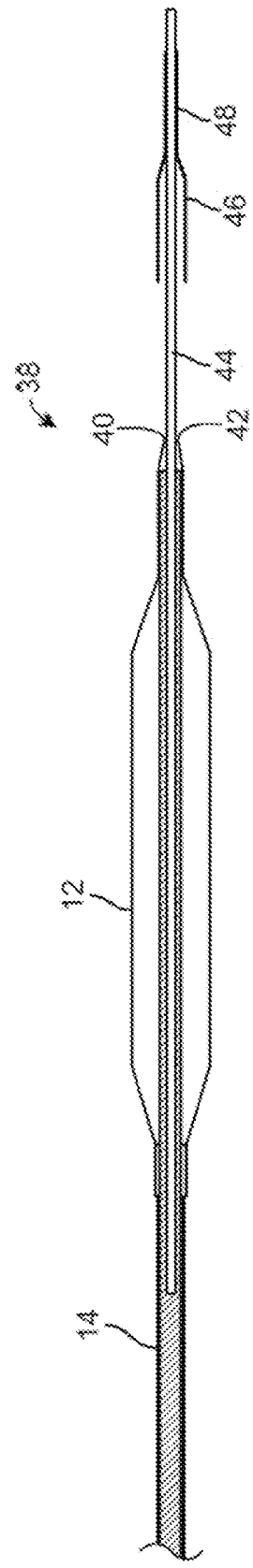
Figure 7C:
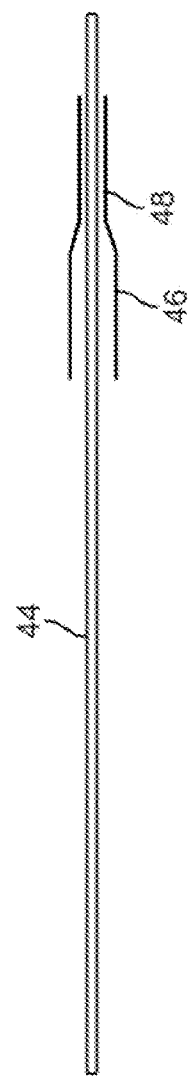
FIG. 7C shows a partial cross-sectional side view of the mandrel assembly having a flared seal for placement over the catheter distal end.

Turning now to FIGS. 7A to 7C, one example of the mandrel assembly 38 for sealing the distal end of the catheter is illustrated. Mandrel 44 may be comprised of a material such as stainless steel which is sized to have a diameter (e.g., having an outer diameter of 0.005 in-0.080 in) which is suitable for insertion within the guidewire lumen 24 of catheter 14. Mandrel 44 may have a length (e.g., 1 cm-160 cm) which is varied so long as the mandrel 44 may extend at least partially through the balloon 12 as the mandrel 44 may provide structural integrity to the catheter 14 during stent crimping upon the balloon 12. The increased structural strength provided by the mandrel 44 to catheter 14 may inhibit or prevent the catheter from buckling as the stent 10 is placed and crimped thereupon.

Seal 46 (which may be comprised of an elastic material such silicone, latex, Pebax®, etc.) may be attached 48 (e.g., via adhesive) near or at a distal end of mandrel 48 and flare proximally such that the seal 46 forms a tubular structure (e.g., having an outer diameter of 0.007 in-0.090 in and an inner diameter of 0.005 in-0.090 in) which may slidingly receive the distal end 42 of the catheter 14 while mandrel 44 is inserted into the guidewire lumen 24. With mandrel assembly 38 securely positioned through the distal opening 40 of catheter 14 and over the distal tip 42, fluid communication is inhibited or prevented between the guidewire lumen 24 and the environment, as shown in FIG. 7A.

Once sterilization is complete and/or prior to the catheter 14 and crimped stent 10 being inserted into the patient, mandrel assembly 38 may be removed by sliding mandrel 44 distally through opening 40 from lumen 24, as shown in FIG. 7B. FIG. 7C illustrates the mandrel assembly 38 completely removed from the catheter 14.

Figure 8A:
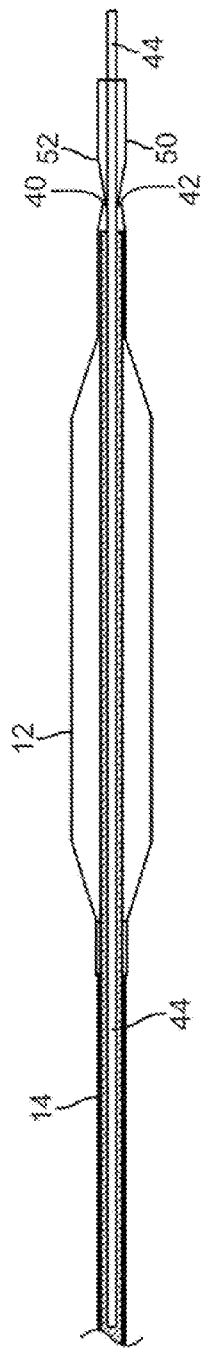
FIGS. 8A and 8B show partial cross-sectional side views of another variation of the mandrel assembly removed from the distal tip of the catheter.
Figure 8B:
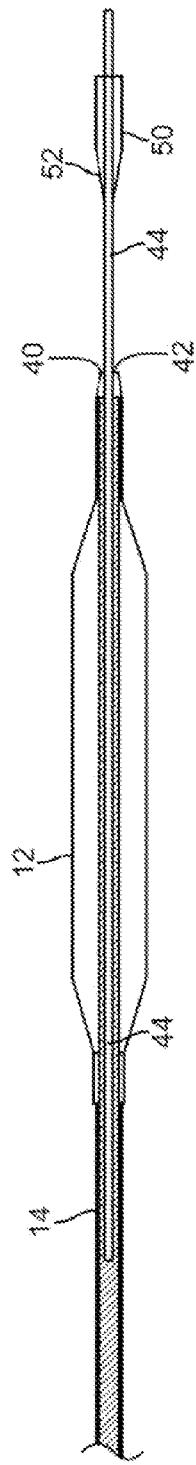
Figure 8C:
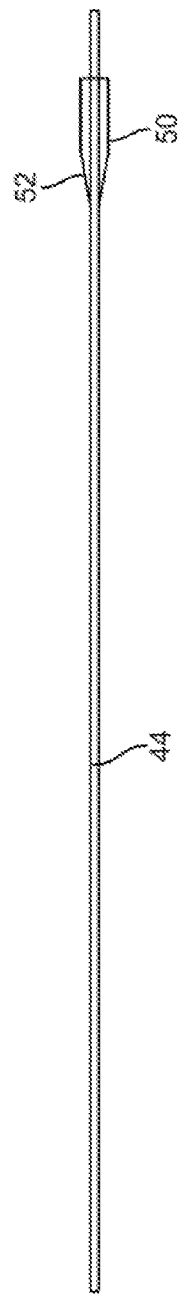
FIG. 8C shows a partial cross-sectional side view of the mandrel assembly having a plug assembly for insertion into the catheter distal end.

Another example of a mandrel assembly is shown in the side views of FIGS. 8A to 8C. In this variation, a plug member 50 having a tapered portion 52 extending, proximally along mandrel 44 may be attached near or at a distal end of mandrel 44. The tapered portion 52 may be inserted into the distal opening 40 as mandrel 44 is slid into the guidewire lumen 24 to effectively plug the catheter tip. The plug member 50 may be comprised of a polymeric material such as silicone. Pebax®, etc. which conforms to the catheter opening 40. FIG. 8B illustrates the mandrel assembly being removed from the guidewire lumen and FIG. 8C shows the mandrel assembly removed entirely from the catheter.

Figure 9A:
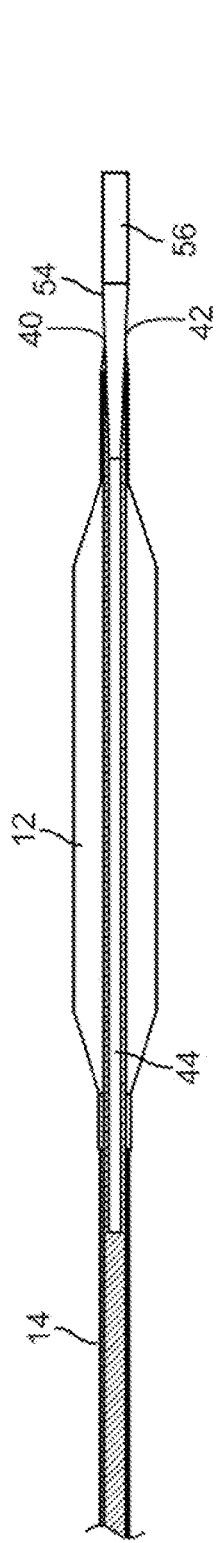
FIGS. 9A and 9B show partial cross-sectional side views of another variation of the mandrel assembly removed from the distal tip of the catheter.
Figure 9B:
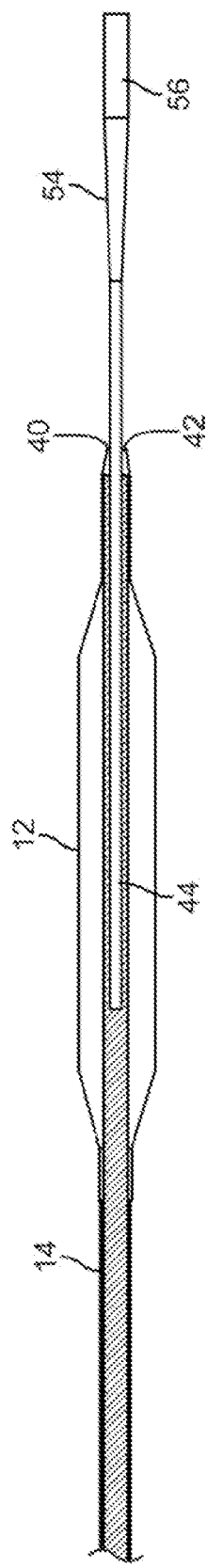
Figure 9C:
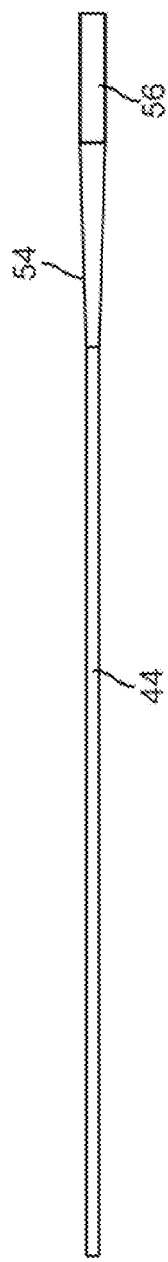
FIG. 9C shows a partial cross-sectional side view of the mandrel assembly having a tapered portion for insertion into the catheter distal end.

FIGS. 9A to 9C show yet another example of a mandrel assembly. In this variation, mandrel 44 may be comprised of a mandrel having, an integrated tapered section 54 extending into a widened section 56 near or at a distal end of the mandrel. The mandrel may be comprised of stainless steel, as above, or a relatively high-durometer polymer, or any other suitable material. FIGS. 9B and 9C illustrate the partial removal of the mandrel and the mandrel completely removed from the catheter.

Turning back now to pre-conditioning and/or sterilization processes, another variation is described which achieves or maintains particular post-sterilization mechanical properties of the stent. The implanted stent 10 may desirably achieve or maintain mechanical characteristics which are either enhanced or at the least unaffected by the sterilization methods. For instance, the stent 10 may achieve or maintain at least one (and desirably all) of the following characteristics, e.g., a diameter increase by 5%-80% via, the inflatable balloon 12 without fracture formation; may curve up to 180° about a 1 cm curvature radius without fracture formation; exhibit a percent reduction in axial length of between 10%-50% without fracture formation when placed under an axial load; exhibit a percent reduction in diameter of between 5%-70% without fracture formation when placed under a compressive load; and exhibit a 20% radial deformation when placed under a load of 0.1 N-5 N.

Depending on the molecular weight and crystallinity combination of the stent materials chosen, the fully sterilized stent may be able to maintain its original crystallinity of 25%-35% and a molecular weight of 259,000 g/mol to 2,120,000 g/mol while providing high radial strength (e.g., 0.1 N-5 N per 1 cm length at 20% compression), withstanding considerable amounts of straw without fracturing (e.g., 150% strain), and exhibiting high fatigue life under physiological conditions (e.g, 10 million cycles under radial pulse load), 200,000-1 million cycles under axial compression and torsional loads.

Examples of steins and methods of processing stents having such mechanical properties which may be produced utilizing the sterilization processes herein are shown and described in further detail in U.S. patent application Ser. Nos. 12/143,659 filed Jun. 20, 2008 and 12/488,453 filed Jun. 19, 2009, each of which is incorporated herein by reference in its entirety.

In yet another variation, the balloon may be inflated and stent mounted onto the inflated balloon prior to pre-sterilization. The assembly may be then sterilized using ETO sterilization with an operating temperature range of 38-50° C. and RH of 20%-80%. The stent may be subsequently crimped on to the balloon in an aseptic or semi-aseptic environment and terminally sterilized by using VHP sterilization. The purpose of pre-sterilization of the inflated balloon is to eliminate the need for inflation during the crimping process, thus reducing the potential for introduction of bacterial load.

In any of the variations herein, the bioabsorbable polymeric stent may be selected from the group consisting, of polyethylene, polycarbonates, polyamides, polyesteramides, polyetheretherketone, polyacetals, polyketals, polyurethane, polyolefin, polyethylene terephthalate, polylactide, poly-L-lactide, poly-glycolide, polylactide-co-glycolide), polycaprolactone, caprolactones, polydioxanones, polyanhydrides, polyorthocarbonates, polyphosphazenes, chitin, chitosan, poly(amino acids), polyorthoesters, oligomers, homopolymers, methyl cerylate, methyl methacrylate, acryli acid, methacrylic acid, acrylamide, hydroxyethy acrylate, hydroxyethyl methacrylate, glycerylscrylate, glyceryl methacrylate, methacrylamide, ethacrylamide, styrene, vinyl chloride, binaly pyrrolidone, polyvinyl alcohol, polycoprolactam, polylauryl lactam, polyjexamethylene adipamide, polyexamethylene dodecanediamide, trimethylene carbonate, poly(β-hydroxybutyrate), poly(g-ethyl glutamate), poly(DTH iminocarbonate), poly(bisphonol A iminocarbonate), polycyanoacrylate, polyphosphazene, methyl cerylate, methyl methacrylate, acryli acid, methacrylic acid, acrylamide hydroxyethy acrylate, hydroxyethyl methacrylate, glyceryl serylate, glyceryl methacrylate, methacrylamide ethacrylamide, and copolymers, terpolymers and combinations and mixtures thereof.

The applications of the disclosed invention discussed above are not limited to certain processes, treatments, or placement in certain regions of the body, but may include any number of other processes, treatments, and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A method for sterilizing a catheter assembly, comprising:
   providing a catheter having a proximal end, a distal end, and at least one lumen therethrough;
   sealing the proximal end of the at least one lumen;
   sealing the distal end of the at least one lumen via an elongate mandrel which is removably inserted into the distal end of the at least one lumen such that the lumen is isolated from an environment;
   sterilizing an interior of the at least one lumen; and,
   sterilizing an exterior of the catheter.

2. The method of claim 1 wherein sterilizing an interior comprises sterilizing via ethylene oxide or radiation.

3. The method of claim 1 wherein sealing the proximal end comprises sealing a guidewire lumen or an inflation lumen.

4. The method of claim 1 wherein sealing the proximal end comprises actuating a stop from an opened to a closed configuration.

5. The method of claim 1 wherein sealing the distal end comprises inserting the elongate mandrel into the distal end of the lumen such that a sealing portion of the mandrel occludes the distal end of the catheter.

6. The method of claim 5 wherein the elongate mandrel comprises a tapered sealing portion which receives the distal end of the catheter in an occluding manner.

7. The method of claim 5 wherein the elongate mandrel comprises a plugging portion which occludes the distal end of the lumen.

8. The method of claim 1 further comprising introducing a gas or fluid into the at least one lumen to at least partially inflate a balloon positioned along the catheter prior to sealing the proximal end.

9. The method of claim 8 wherein the gas or fluid is introduced into the at least one lumen through at least one corresponding filter such that sterility of the lumen is maintained.

10. The method of claim 9 further comprising crimping a stent upon the balloon.

11. The method of claim 10 further comprising removing the at least one filter.

12. The method of claim 11 further comprising introducing the catheter intravascularly into a patient body to a vascular region to be treated.

13. The method of claim 12 further comprising expanding the stent via the balloon to deploy stem.

* * * * *

UNITED STATES PATENT AND TRADEMARK OFFICE
CERTIFICATE OF CORRECTION

| | | |
|---|---|---|
| PATENT NO. | : 8,574,493 B2 | Page 1 of 1 |
| APPLICATION NO. | : 13/671211 | |
| DATED | : November 5, 2013 | |
| INVENTOR(S) | : Kamal Ramzipoor et al. | |

It is certified that error appears in the above-identified patent and that said Letters Patent is hereby corrected as shown below:

In the Specification:
In column 1, line 27, please replace "formers" with --thrillers--.
In column 1, line 64, please replace "to" with --a--.
In column 2, line 38, please replace "UFO" with --ETO--.
In column 2, line 57, please replace "Md." with --MD--.
In column 3, line 31, please replace "or" with --of--.
In column 3, line 33, please replace "slops" with --stops--.
In column 3, line 42, please replace "tell" with --left--.
In column 3, line 43, please replace "liter" with --luer--.
In column 4, line 57, please replace "liter" with --luer--.
In column 4, line 59, please replace "far" with --for--.
In column 5, line 2, please replace "dosed" with --closed--.
In column 5, line 28, please replace "stems" with --stents--.
In column 5, line 43, please replace "strut" with --stent--.
In column 6, line 11, please replace "strut" with --stent--.
In column 6, line 19, please replace "Md." with --MD--.
In column 9, line 14, please replace "steins" with --stents--.
In column 9, line 36, please replace "polylactide-co-glycolide" with --poly (lactide-co-glycolide)--.
In column 9, line 42, please replace "glycerylscrylate" with --glyceryl scrylate--.
In column 9, line 48, please replace "bisphonol" with --bisphenol--.
In column 9, line 52, please replace "serylate" with --scrylate--.

In the Claims:
In claim 13, column 10, line 56, please replace "stem" with --stent--.

Signed and Sealed this
Twenty-fifth Day of February, 2014

Michelle K. Lee
*Deputy Director of the United States Patent and Trademark Office*